United States Patent [19]
Turner

[11] Patent Number: 5,624,438
[45] Date of Patent: Apr. 29, 1997

[54] RETINAL WIDE-ANGLE ILLUMINATOR FOR EYE SURGERY

[76] Inventor: R. Scott Turner, 620 Carpenter La., Philadelphia, Pa. 19119

[21] Appl. No.: 239,865

[22] Filed: May 9, 1994

[51] Int. Cl.⁶ .................................................. A61N 5/06
[52] U.S. Cl. ........................... 606/15; 606/4; 606/17; 600/101; 362/32; 362/800
[58] Field of Search .................... 606/2, 4–7, 10–17; 362/32, 800; 128/4–6; 600/101

[56] References Cited

U.S. PATENT DOCUMENTS

| | | | |
|---|---|---|---|
| 4,648,892 | 3/1987 | Kittrell et al. | 606/7 |
| 4,669,818 | 6/1987 | Myer | 607/93 |
| 4,686,979 | 8/1987 | Gruen et al. | 606/4 |
| 4,860,743 | 8/1989 | Abela | 606/7 |

*Primary Examiner*—David M. Shay
*Attorney, Agent, or Firm*—Charles I. Brodsky

[57] ABSTRACT

The illuminator of the invention takes relatively coherent light exiting from a fiber optic cable, and disperses it in an even manner over a wide viewing area of an eye retina, and by securing a transparent material having a light dispersing first surface to face the light output end of the fiber optic cable with an air gap in-between, thus allowing a large light index differential between the fiber material and the light dispersing material.

8 Claims, 1 Drawing Sheet

RETINAL WIDE-ANGLE ILLUMINATOR FOR EYE SURGERY

FIELD OF THE INVENTION

This invention relates to eye surgery, in general, and to a light-dispersing illuminator to spread the light out over the eye retina, in particular.

BACKGROUND OF THE INVENTION

As is well known and understood, in retinal eye repair surgery, it is very highly desirable for the surgeon to view as much of the retina as possible. Wide-angle viewing objective lenses have been developed by microscope manufacturers to aid in this. However, and because of back-reflected light, the illumination of the retina cannot generally be had through the same microscope lens. As a result—and as is also understood—, an opening is thus made in the eye, where a fiber optic cable is then inserted that provides a beam of light to illuminate the retinal area.

A significant problem with such an arrangement was recognized when it was realized that the largest fiber optic beam that could be obtained was only of the order of 0.25 inches in diameter; thus, attempts at increased beam-spreading the relatively coherent light were tried. Such attempts proved highly unsuccessful in practice, though, especially when placing a lens on the end of the fiber optic cable—as analysis showed that providing any type of light refracting lens on the surface of the fiber optic cable was for the most part cancelled out, and due to the light refracting index matching of the vitreous eye fluid to that of the light refracting lens material which came in contact with such fluid. It was also found that making and aligning very small lenses was very difficult. Additional approaches to overcome this problem also prove of limited usefulness in that the light spreading that is achieved is essentially omnidirectional—i.e. spread 360°—, instead of being focused in the retinal area of concern. Additionally, and because such approaches provide a near 360° omni-directional angle of dispersion, it was determined that a significant portion of the light being spread also is directed back through the eye lens and microscope lens through which the surgeon viewed the retina, thus producing a glare. Also, valuable light is dispersed onto areas where no viewing can be achieved.

OBJECTS OF THE INVENTION

It is an object of the present invention, therefore, to provide a new and improved wide-angle illuminator for use in retinal eye surgery.

It is another object of the invention to provide such an illuminator which is light-efficient, and which throws a minimum amount of light back into the viewing path of the microscope lens.

It is a further object of the invention to provide such a wide-angle illuminator inexpensively, and in a manner which allows the fiber optic light to be dispersed in a manner of optimum light refraction angle.

SUMMARY OF THE INVENTION

As will become clear from the following description, the retinal illuminator of the present invention allows for the satisfaction of these objectives by taking relatively coherent light exiting from the fiber optic cable and dispersing it in an even manner over the viewing area of the retina by placing a transparent material having a light dispersing first surface facing the light output end of the fiber optic cable in air, thus allowing a large light index differential between the fiber material and the light dispersing material. As will be seen, in a preferred embodiment incorporating the principles of the invention, the fiber optic cable is inserted within a support tube of a handpiece stem, with the support tube extending a portion beyond the light output end of the cable; a transparent material is secured within the extending portion of the support tube, in this embodiment, having a light dispersing first surface which faces the light output end of the fiber optic cable, with an air gap between such first surface and the cable's light output end. To prevent the refracting index of the vitreous eye fluid from affecting the light dispersion which results, the apparatus of the invention will also be seen to incorporate a seal about the transparent material, between it and the inside surface of the support tube.

As will become clear from the following description, the light dispersing first surface of the transparent material may comprise, in this preferred embodiment of the invention, a holographic surface relief of random micro-lenses, embossed on a medical grade acrylic, for example, to provide a refracted coherent light at predetermined angles, and of the order of 100°.

BRIEF DESCRIPTION OF THE DRAWING

These and other features of the present invention will be more clearly understood from a consideration of the following description, taken in connection with the accompanying drawing, in which.

DETAILED DESCRIPTION OF THE DRAWING

Figure 1:
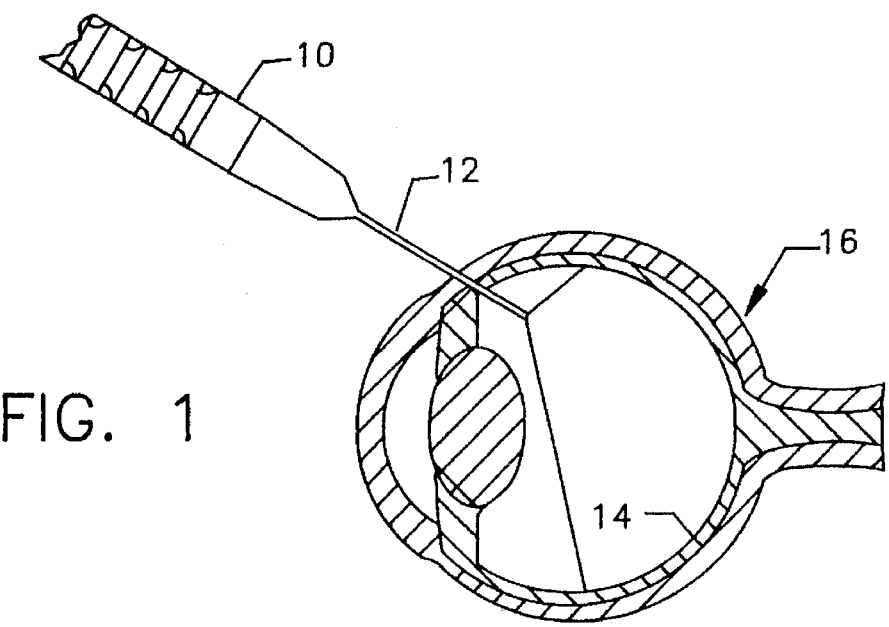
FIG. 1 is a pictorial illustration of a handpiece stem inserted into the eye to illuminate the retina, helpful in an understanding of the invention.

In FIG. 1, a handpiece 10 typically delivers a beam of relatively coherent light through a stem 12 to illuminate the retina 14 of the eye, generally shown at 16. As will be understood, such collimated beam is generated by any appropriate light source 18 (FIG. 2) and delivered to illuminate the retina 14 by means of a coupling system 20 including a fiber optic cable which passes through the handpiece stem 12. In accordance with a preferred embodiment of the invention, the fiber optic cable used herein is selected of a diameter of the order 0.029 inch and less, and is illustrated by the reference notation 22 in FIG. 3. Such fiber optic cable is usually encased within a support tube 24 of slightly larger inside diameter—0.030 inch for the preferred embodiment of the invention being described. As will be understood by those skilled in the art, it would be highly desirable to spread the light beam over as much of the surface of the retina 14 as the microscope wide angle objective lens makes as possible, yet without directing any source light back through the microscope lens being used by the eye surgeon.

Figure 3:
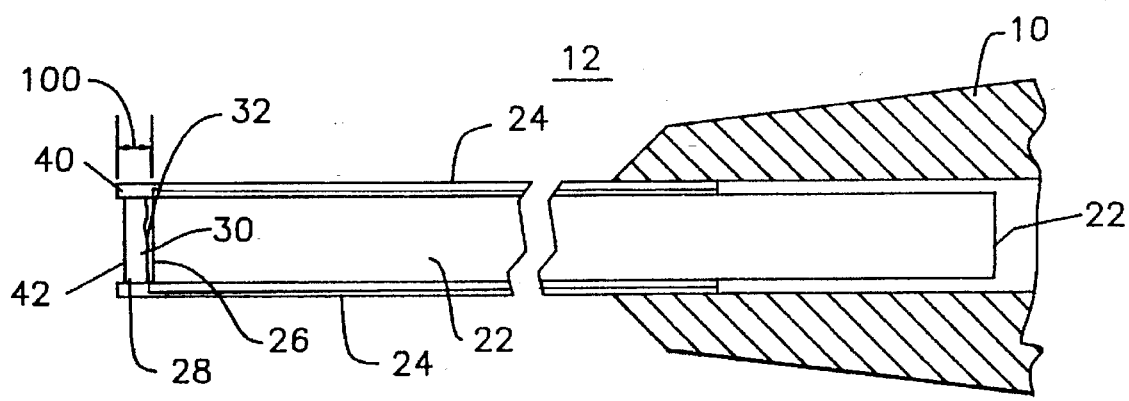
FIG. 3 is a cross-section schematic view of the stem of FIG. 1, constructed in accordance with the present invention.

Thus, and according to the invention, the support tube 24 of FIG. 3 extends a portion 100 beyond the end of the fiber optic cable, shown at 26, —understood as being the "light output end" of the fiber optic cable 22. To achieve a focused beam spreading, a transparent material 28 is included, within the extending portion 100 of the support tube 24, and of a thickness less than the amount of the support tube extension 100. More particularly, such transparent material 28 is selected to have a light dispersing first surface 30 facing the light output end 26 of the fiber optic cable 22, and with an air gap 32 between the surface 30 and the end 26. Such transparent material 28 preferably incorporates a holographic surface relief of random micro-lenses at the surface 30, to refract coherent light at predetermined angles according to its manufacture, of the order of 100° (or somewhat less, determined as a trade-off between the amount of area over which the collimated light is to be spread in connection with the drop-off in the light intensity as increasing angles of beam spread are selected). Such transparent material 28 may comprise an embossed medical grade material—chosen, for example, from the class of acrylic, optical grade epoxies, polycarbonates and polystyrenes. Such material will be seen of a resilient composition, and, in accordance with the invention, is held within the extending portion 100 of the support tube 24 by a press fit in providing a seal against vitreous eye fluids from reaching the air gap 32. To effectuate this, the transparent material 28 is fabricated of a diameter of the order of 0.001 inch larger than the inner diameter of the support tube 24—and of the order of 0.031 inch, for example, when the support tube 24 has an inside diameter of the order of 0.030 inch.

As will be appreciated, by placing the transparent material 28 with its light dispersing first surface 30 facing the light output end 26 of the fiber optic cable 22 in the air gap 32, a large light index differential is established between the fiber material and the light dispersing surface and gives rise to a light dispersal in a manner of optimum light refraction, without any index switching or changing because of the vitreous eye fluid. As will be apparent, this essentially follows because the vitreous fluid in the eye does not contact the light refracting surface of the light spreading material. By selecting the diameter of the transparent material 28 in this respect to be larger than the inside diameter of the support tube 24, an effective seal is provided around the material 28 in preventing the vitreous eye fluids from reaching the air gap 32. To further hold the transparent material 28 secured in position within the support tube 24, FIG. 3 illustrates the ends of the support tube 24 essentially being rolled-over (as at 40) about a second surface 42 of the transparent material 28, opposite to the light dispersing surface 30.

Figure 2:
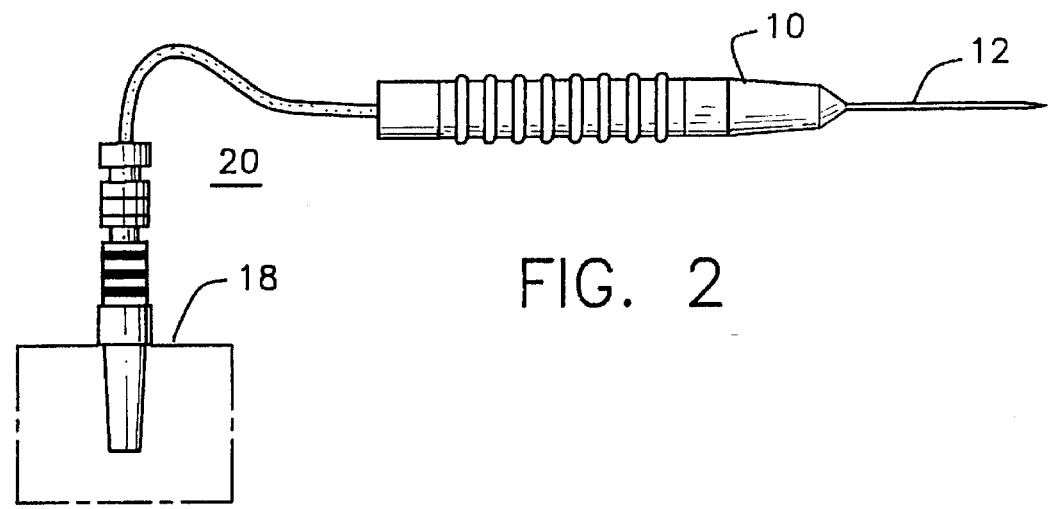
FIG. 2 is a pictorial illustration of a cable assembly for delivering a relatively coherent light through the stem of FIG. 1.

With the light source 18 of FIG. 2 comprising a halogen light bulb and a condensing lens, for example, the illuminator of the invention will then be effective to enable the eye surgeon to direct the light to substantially cover where he wishes in illuminating a retinal area. By specifying the dispersal angle desired, a hologram can be developed for transforming into the random micro-lenses to obtain this—either with, or without, a small degree of light "spill-over", along with its concomitant relatively small amount of light-dimming at the edges. In either event, the end result is a construction which throws a minimum amount of light back into the viewing path of the surgeon's microscope lens, and in a construction which is quite inexpensive to produce.

While there have been described what are considered to be preferred embodiments of the present invention, it will be readily appreciated by those skilled in the art that modifications can be made without departing from the scope of the teachings herein. Thus, and for example, while the wide-angle illuminator of the invention has been particularly described in context with a manner of employing it to advantage in retinal eye surgery, the teachings of the invention will apply whenever it is desired to provide light dispersal inside a body over a wide angle, as in bladder surgery. There, and generally in any type of environment where transparent fluids would interfere with obtaining a wide-angle illumination, a handpiece stem could be utilized, according to the invention, in allowing a large light index differential between the fiber material and light dispersing material, to invasively illuminate inside the body at close proximity regardless of the relatively transparent fluid present where the handpiece stem is immersed. Additionally, and as will be understood, the teachings of the invention could apply equally as well in these or other procedures—even without the need of a handpiece, as where the wide angle illuminator is located on the end of an endoscope, for example. For such reason, therefore, the scope of the present invention should be read in light of the appended claims which describe the apparatus for providing this light dispersal, and the method of obtaining this type of invasive illumination, not only within the eye, but at any point within the body.

I claim:

1. In a stem to illuminate the retina of an eye, apparatus comprising:

a fiber optic cable within said stem having a light output end delivering coherent light;

a support tube, having an inner diameter and an outer diameter, surrounding said fiber optic cable and and extending a portion beyond said light output end of said fiber optic cable;

a transparent thin disc material within said extending portion of said support tube, with said transparent material having a light dispersing straight-sided first surface facing said light output end of said fiber optic cable; and an air gap between said light dispersing first surface of said transparent material and said light output end of said fiber optic cable; and wherein said transparent material is held within said extending portion of said support tube by a press-fit to provide a seal about said transparent material for preventing vitreous eye fluids from reaching said air gap;

wherein said transparent material is of a diameter 0.001 inch larger than said inner diameter of said support tube to provide said press-fit; and wherein said transparent material is of a thickness of 0.010 inch.

2. The apparatus of claim 1, wherein said fiber optic cable is of 0.029 inch diameter, wherein said support tube is of 0.030 inch inner diameter, and wherein said transparent material is 0.031 inch diameter.

3. The apparatus of claim 1 wherein said transparent material also includes a straight-sided second surface opposite to said light dispersing straight-sided first surface, and wherein said support tube is rolled over said second surface of said transparent material.

4. The apparatus of claim 1 wherein said light dispersing first surface of said transparent material comprises a holographic element of random micro-lenses.

5. The apparatus of claim 4 wherein said random micro-lenses are selected to refract coherent light at predetermined angles.

6. The apparatus of claim 5 wherein said random micro-lenses are selected to refract coherent light at an angle of 90°.

7. The apparatus of claim 4 wherein said transparent material comprises an embossed medical grade material.

8. The apparatus of claim 7 wherein said transparent material comprises an embossed medical grade material selected from the class of acrylic, optical grade epoxies, polycarbonates and polystyrenes.

* * * * *